United States Patent [19]

Veragen

[11] Patent Number: 4,516,567
[45] Date of Patent: May 14, 1985

[54] SEQUENTIAL PNEUMATIC CONTROL DEVICE, SUPPLIED WITH ELECTRIC ENERGY

[75] Inventor: René Veragen, Chatou, France

[73] Assignee: Sagem, Paris, France

[21] Appl. No.: 516,889

[22] Filed: Jul. 25, 1983

[30] Foreign Application Priority Data

Jul. 26, 1982 [FR] France .................... 82 13007

[51] Int. Cl.³ ............................................. A61M 1/03
[52] U.S. Cl. ........................................ 128/1 D; 3/1.7
[58] Field of Search ...................... 128/1 D; 3/1.7; 417/44–46

[56] References Cited

U.S. PATENT DOCUMENTS

| | | | |
|---|---|---|---|
| 3,966,358 | 6/1976 | Heimes et al. | 3/1.7 X |
| 4,173,796 | 11/1979 | Jarvik | 3/1.7 |
| 4,185,617 | 1/1980 | Hutchins | 128/1 D |
| 4,222,127 | 9/1980 | Donachy et al. | 128/1 D X |

OTHER PUBLICATIONS

Geisselbrecht et al., "Implantable Driving System ... ", *Biomedizinische Technik,* vol. 19, No. 6, pp. 217-224, Dec. 1974.

Primary Examiner—Edward M. Coven
Attorney, Agent, or Firm—Larson & Taylor

[57] ABSTRACT

The invention relates to a sequential pneumatic control device, supplied with electric energy, for a total cardiac prosthesis (4) formed by a biventricular monobloc assembly with pneumatic operation, this device being contained in at least one sealed case (10) implantable in the human body; this device comprises an enclosure forming a drive fluid reserve defined by a wall at least partially flexible (12) subjected to the internal pressure of the human body, whereby the initial pressure of the drive fluid is made permanently dependent on said internal pressure of the body, which serves as a reference pressure.

8 Claims, 6 Drawing Figures

SEQUENTIAL PNEUMATIC CONTROL DEVICE, SUPPLIED WITH ELECTRIC ENERGY

The present invention relates to a sequential pneumatic control device, supplied with electric energy, with pneumatic operation, especially for a total cardiac prosthesis formed by a biventricular monobloc assembly, with pneumatic operation, this device being housed in at least one rigid case able to be implanted in the human body and comprising an enclosure forming a drive gas reserve defined by a wall at least partially flexible subjected to the internal pressure of the human body.

A device of the above-mentioned kind is already known, however with hydraulic operation, in which the flexible wall enclosure forming a drive fluid reserve is in the form of an assembly separate from the drive part. Positioning of the device requires then implantation, in separate locations, of the drive part, on the one hand, and of the deformable enclosure on the other, these two elements being functionally connected together and to the cardiac prosthesis. Such an assembly is described for example in U.S. Pat. No. 4,173,796.

Such an arrangement leads to implanting in the body a number of elements which may, it is true, have relatively small individual volumes but whose overall volume is considerable.

Knowing this state of the art relative to sequential control devices for hydraulic operation cardiac prostheses, it has then seemed desirable to design a sequential control device for a pneumatic operation cardiac prosthesis overcoming the main disadvantage mentioned above.

To this end, the sequential pneumatic control device in accordance with the invention is characterized in that the rigid case is in the form of an open rigid case and in that the gas reserve is formed partly by said open rigid case and partly by a flexible pocket covering the open case and connected thereto in a gastight way.

With this arrangement, the advantage is maintained of the presence of a flexible wall which communicates directly to the drive gas the internal pressure of the human body and which allows a pressure reference to be formed with certainly, reliably and inexpensively which is automatically adapted to the ambient pressure (for example depending on the altitude) in which the wearer of the prosthesis is plunged.

With this advantage is associated another advantage which is the construction of the device in monobloc form which is easier to implant, with a further additional advantage which is the reduction of the overall volume of the implanted elements; this reduction results from the incorporation, in the volume of the enclosure forming a drive gas reserve, of the inner volume of the case containing the pneumatic control apparatus, which volume forms a dead volume or useless volume if it were not used as specified in accordance with the invention.

Preferably, support means are provided for maintaining the flexible wall or the flexible part of the wall of the reserve extended when the amount of gas contained in the reserve is low, so that the wall may be freely deformed, even after a long period during which the volume of the reserve has varied little (e.g. at constant altitude).

In one embodiment, the device of the invention comprises:

a pneumatic pump,
at least one main valve for distributing the pressurized fluid delivered by the pump,
at least one electric motor for actuating said valve,
a reference pressure detector,
a detector of at least one functional condition,
and control means whose inputs are connected to said reference pressure and functional condition detectors and whose outputs are connected to the pneumatic pump and to the valve motor.

Advantageously, in this case, the control means are electronic and the detectors are adapted to deliver electric signals.

To save space, the means for supporting the flexible wall comprise a rigid or semi-rigid dividing wall and the electric circuits of the device are carried by this dividing wall, formed more especially by a printed circuit board.

Advantageously, an auxiliary valve controlled by the control means is connected in parallel across the main valve for cyclically connecting the pneumatic circuit supplying the total cardiac prosthesis to the gas reserve.

The invention will be better understood from reading the detailed description which follows of some embodiments given solely by way of non limiting examples. In this description, reference is made to the accompanying drawings in which.

Figure 1:
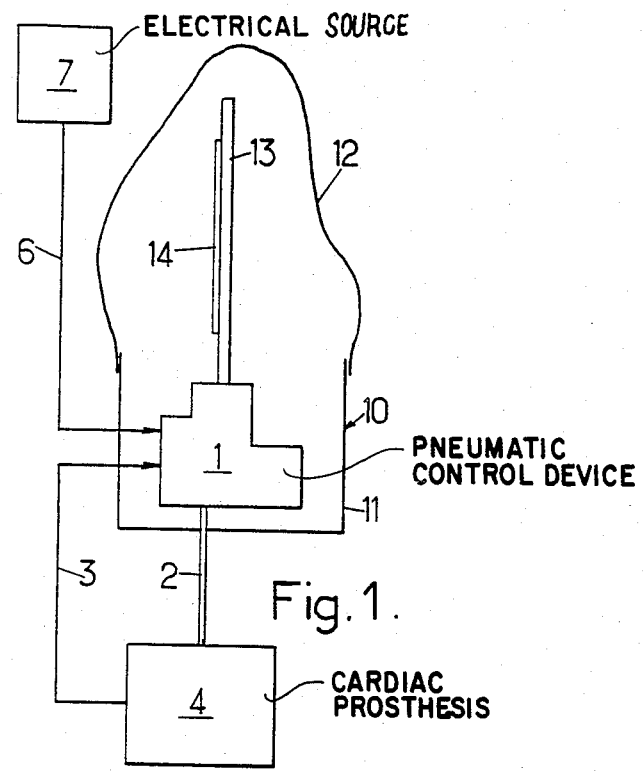
FIG. 1 is a schematical representation of a sequential pneumatic control device constructed in accordance with the invention.

In FIG. 1, a sequential pneumatic control device 1 is intended to control, through at least one pneumatic duct 2 and a servo-control loop 3, a pneumatic operating cardiac prosthesis 4, which may be a total cardiac prosthesis formed by a pneumatic operation biventricular monobloc assembly, such for example as the prosthesis described in the patent application FR 79 01529 (published under the no. 2,446,631) and its addition FR 79 29365 (published under the no. 2,470,593).

The device 1 is contained in a sealed assembly 10 which is adapted (more especially as its shape and the nature of the material forming it are concerned) to be implanted in the human body, in the same way as the total cardiac prosthesis 4. Thus, the density of the device-case assembly must be substantially the same as that of the region of the body (pulmonary zone) in which it will be positioned.

The device 1 is supplied with electric energy, through a connection 6, from an electric energy source 7 which is either external to the human body in the case where it is formed from batteries or a battery of conventional accumulators whose weight is relatively high (too high to be implanted inside the body), or inside the human body in the case where it is formed from very lightweight generating elements.

For the operation of the sequential pneumatic control device 1, it is necessary to associate therewith a drive gas reserve. To reduce the space generally occupied by the device and to facilitate implantation thereof in the human body, the monobloc assembly 10 is formed, as shown in FIG. 1, partly with a rigid wall 11, partly with a flexible wall 12, connected sealingly together. In other words, the free space available inside the open case with rigid wall 11 is used as drive gas reserve.

It will be noted that it is desirable for the flexible wall 12 to be able to be deformed freely, even after a long period during which the volume of the reserve has varied little (e.g. if the wearer of the prosthesis remains at a constant altitude). To this end, a support member is provided extending inside the flexible part. By way of example, as shown in FIG. 1, it is advantageous so as not to increase the number of component parts of the device and not to increase its weight, for said support member to be quite simply formed by a plate 13, more especially wholly or partly by a printed circuit board, fixed to the mechanical part of the sequential pneumatic control device 1 and supporting the whole of the electronic part 14 and possibly other parts, required for monitoring and/or controlling device 1.

A number of particular embodiments will now be described, shown in FIGS. 2 to 5, which form variants of the embodiment of FIG. 1.

In FIGS. 2 to 5, the device is then incorporated in a monoblock assembly 10 with a partly rigid 11, partly flexible 12 wall, forming the drive gas reserve maintained permanently at the internal pressure of the body because of the flexible wall 12. However, for the sake of clarity of the drawings and to allow a functional representation of some monitoring and/or control blocks, more especially electronic, which, as was mentioned above, are preferably disposed on a printed circuit board 13, serving at the same time as a support for the flexible wall 12, said printed circuit board has not been shown.

Figure 2:
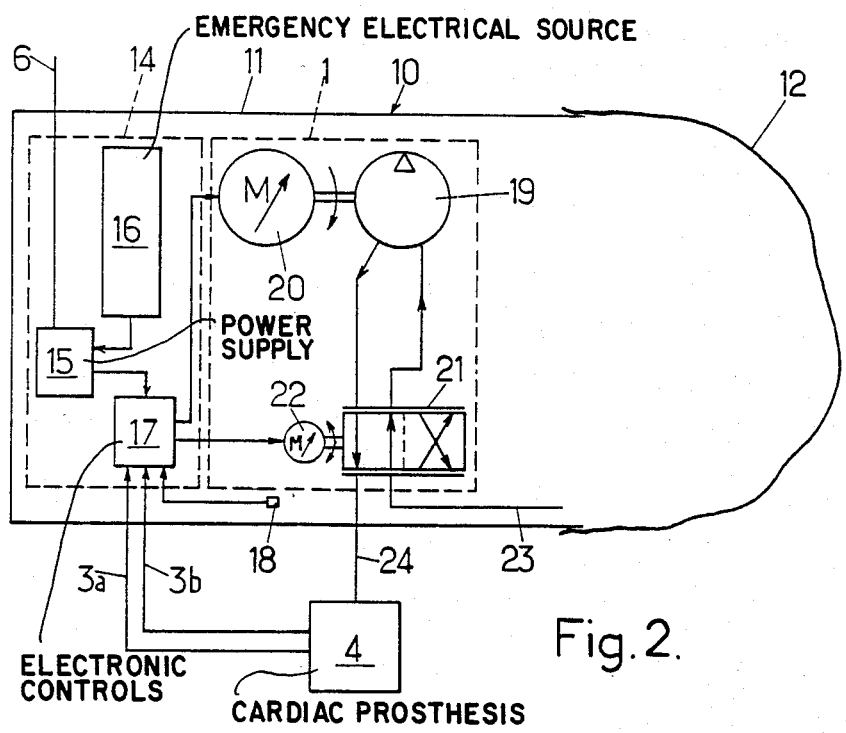
FIGS. 2 to 5 are diagrams of different possible variants of the device of FIG. 1.

In FIGS. 2 to 5, the parts identical to those of FIG. 1 are designated with the same numerical references. Referring first of all to FIG. 2, the electronic part 14 comprises first of all an electric power supply 15 connected, on the one hand, to the external source 7 (not shown) and, on the other hand, to an internal emergency source 16. Since the external source 7 may have different characteristics (DC electric source, AC electric source such as the mains at a frequency of 50 or 60 Hz), the power supply 15 comprises all the rectifying means, all the voltage dropping means, all the means for automatically switching from DC source to AC source and external source to internal emergency source, which are required for ensuring permanently and substantially without discontinuity the supply of electric energy adequate for the operation of the device of the invention.

Preferably, power supply 15 also comprises a battery charging device connected to source 16 and maintaining this latter in the fully charged condition as long as the electric energy is supplied from the external source 7.

The output of the power supply 15 is connected to the power input of a sequential control electronic device 17, which has in addition three data inputs: two inputs, connected to the total cardiac prosthesis 4 by connections 3a and 3b, receive the pressure data respectively from the right ventricle and the left ventricle of the prosthesis and the third input receives the pressure data (serving as reference pressure) from the drive gas reserve, which data is provided by a sensor 18.

The pneumatic part 1 of the device of the invention comprises a pneumatic pump 19 driven by an electric motor 20. A rotary pneumatic distributor 21 of the two position (direct connections and crossed connection) and two circuit type, driven by an electric motor 22, connects pump 19, on the one hand, through one of the circuits to the drive gas reserve (connection 23) and, on the other hand, through the other circuit to the cardiac prosthesis 4 (connection 24).

The electric motor 20 of the pneumatic pump 19 and the electric motor 22 of the rotary distributor 21 are connected to the respective outputs of the sequential control electronic device 17.

The sequential control electronic device 17 delivers the electric energy to motors 20 and 22 sequentially depending on the data arriving at its inputs so that the operating rate of the cardiac prosthesis thus controlled is adapted to the living requirements of the wearer of the prosthesis (physical effort, variation of altitude, etc . . . ).

The device which has just been described and which is shown in FIG. 2, offering only one way of utilization, is suitable for controlling a total cardiac prosthesis of the mono-activated type, i.e. in which the two ventricles have a common wall formed by a single membrane requiring a single activation source.

On the other hand, referring to FIGS. 3 to 5, devices will now be described in accordance with the invention arranged for controlling a total cardiac prosthesis of the bi-activated type, i.e. in which the two ventricles each have an activation membrane, which requires then two sources of activation substantially in phase opposition.

Figure 3:
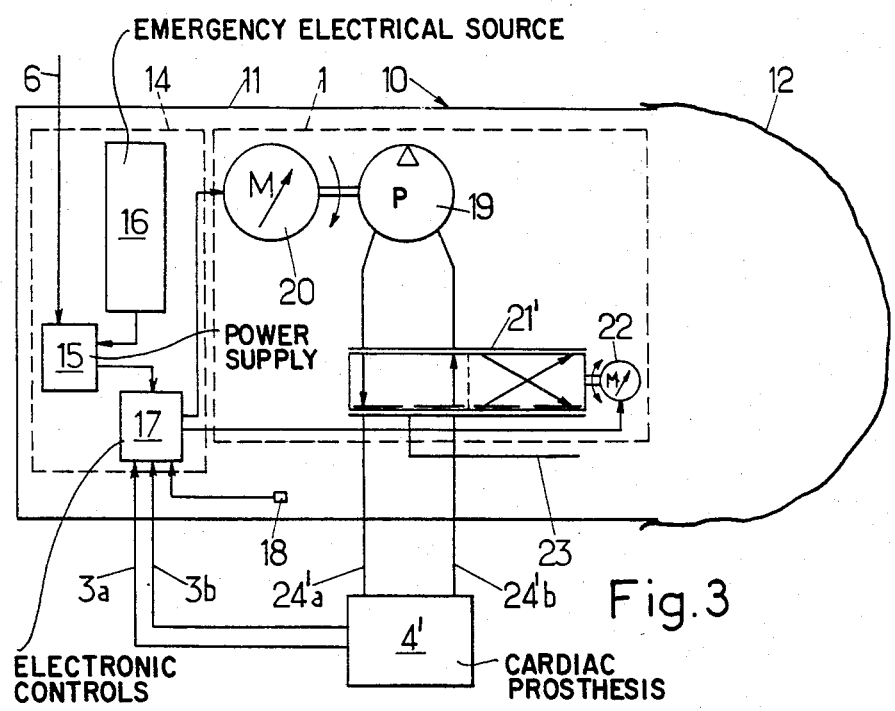
Figure 4:
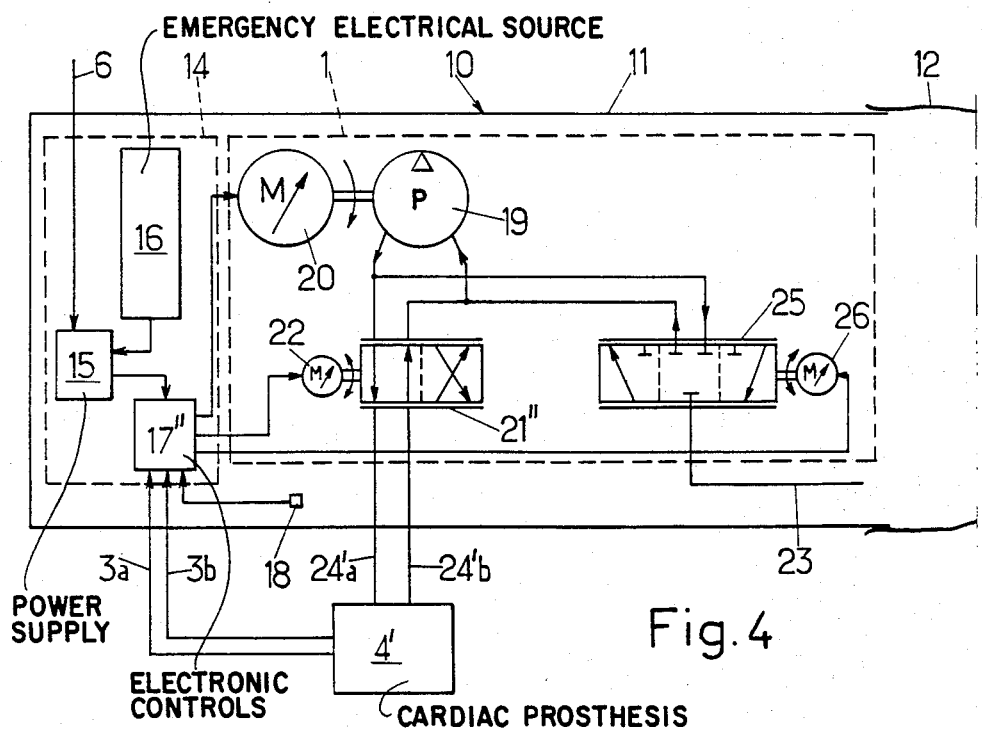
Figure 5:
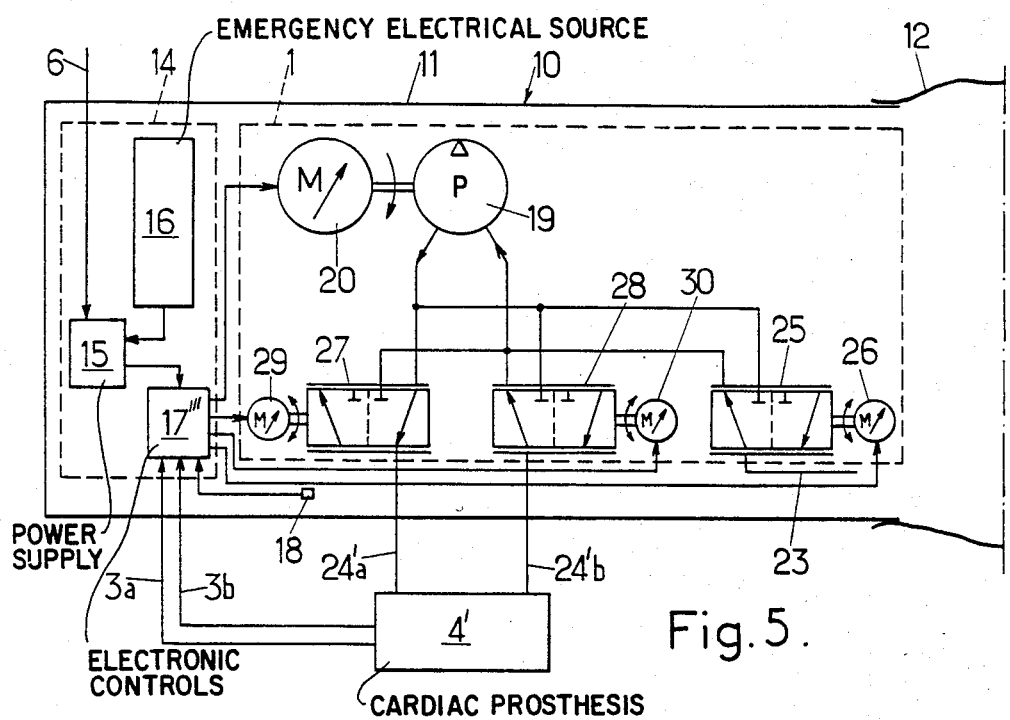

The devices shown in FIGS. 3 to 5 have a general structure substantially similar to that of the device of FIG. 2; the same numerical references are then kept for designating identical parts, the parts of different structure but functionally identical keeping the same numerical reference to which ', ", '" have been added respectively in FIGS. 3, 4 and 5.

The device shown in FIG. 3 comprises a two position (direct and crossed) and two circuit rotary distributor 21' with a mid point connected to the tank (drive gas reserve); these two circuits connect the pump respectively to the two pneumatic chambers which are associated respectively with two ventricles of the bi-activated cardiac prosthesis 4' (connection 24'a and 24'b).

The device shown in FIG. 4 comprises a two position (direct and crossed) rotary distributor 21" with two circuits connecting pump 19 respectively through connections 24'a and 24'b, to the two pneumatic chambers of the bi-activated cardiac prosthesis 4'.

A second rotary distributor 25, driven by a motor 26, is connected in parallel with distributor 21" to the input and output terminals of pump 19. Distributor 25 has three positions and allows the tank (drive gas reserve) to be connected to one or other of the input or output terminals of pump 19, with a further central neutral position.

In addition, the sequential control electronic device 17" has a third output connected to the motor 26 of the second distributor for the sequential control thereof.

The role of the pneumatic distributor 25 is to put the input or the output of pump 19 cyclically in communication with the gas reserve, so as to create a slight depression at the level of the ventricular membranes for facilitating the input of blood into the cardiac prosthesis.

Finally, the device shown in FIG. 5 is formed in the same way as that of FIG. 4, except that the distributor 21" of FIG. 4 is here replaced by two distributors 27 and 28 disposed respectively in the two channels connecting pump 19 to the cardiac prosthesis. Taking into account the arrangement obtained, the three distributors 25, 27 and 28 may be identical and formed by rotary two position distributors, distributors 27 and 28 being driven respectively by two motors 29,30 connected respectively to two separate outputs of the sequential control electronic device 17'''.

Of course, in all the embodiments which have just been described, the rotary distributors may be repaced wholly or partly by spool valves, the choice being guided by different factors (reliability, cost price, approach to operation the nearest possible to nature, etc . . . ).

In so far as the sequential control electronic device is concerned (device 17 of FIG. 2, 17 of FIG. 3, 17'' of FIG. 4 and 17''' of FIG. 5), its operation depends on the cardiac prosthesis used; but, whatever this latter may be, it measures the difference between each ventricle and the ambient reference pressure, it compares these pressure differences with minimum and maximum values which it has stored, and it determines the speed of the motor 20 of pump 19 and the position of motor 22 of distributor 21.

Figure 6:
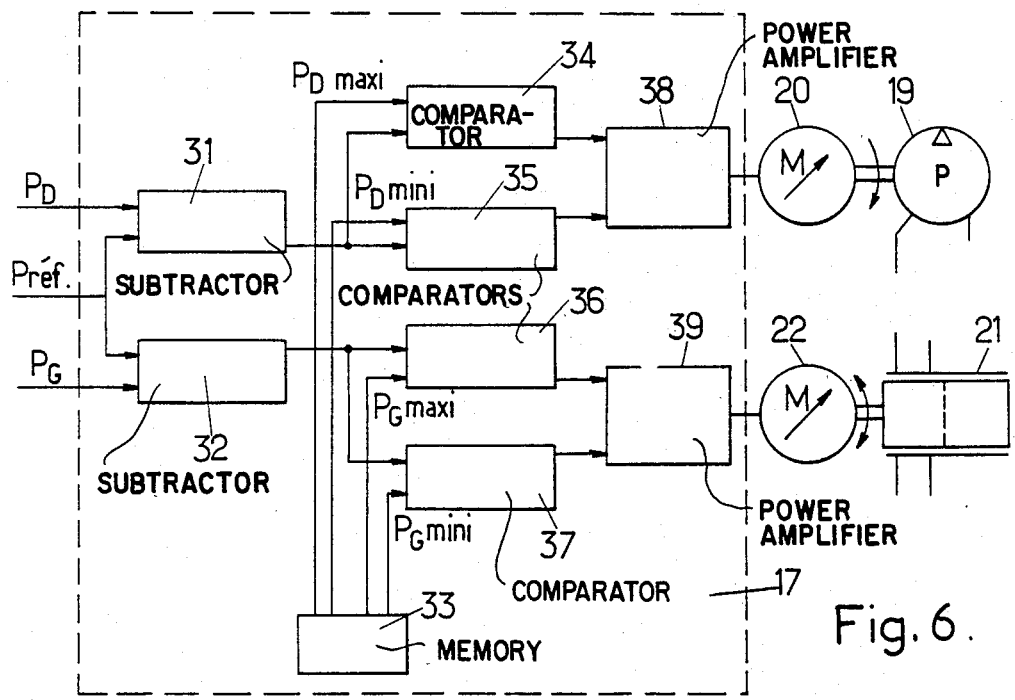
FIG. 6 is a block diagram of the electronic control device forming part of the embodiment of FIG. 2.

By way of purely illustrative example, FIG. 6 shows, in the form of a block diagram, one embodiment of the sequential control electronic device 17 of FIG. 2.

Device 17 comprises two subtractors 31,32 each having two inputs: the inputs of subtractor 31 receive respectively electric signals representative of the pressure $P_D$ in the right ventricle and the reference pressure $P_{ref}$, whereas the other inputs of subtractor 32 receive respectively electric signals representative of the pressure $P_G$ in the left ventricle and of the reference pressure $P_{ref}$.

Device 17 also comprises a memory 33 holding admissible minimum and maximum values for the pressures in the right and left ventricles.

Four comparators 34 to 37 adapted to compare the pressure differences with the stored values are also provided; in other words:

the two inputs of comparator 34 are connected respectively to the output of subtractor 31 and to the output terminal of memory 33 supplying a signal representative of the maximum admissible pressure in the right ventricle $P_{D\ maxi}$;

the two inputs of comparator 35 are connected respectively to the output of subtractor 31 and to the output terminal of memory 33 supplying a signal representative of the minimum admissible pressure in the right ventricle $P_D$ mini;

the two inputs of comparator 36 are connected respectively to the output of subtractor 32 and to the output terminal of memory 33 supplying a signal representative of the maximum admissible pressure in the left ventricle $P_{G\ maxi}$;

the two inputs of comparator 37 are connected respectively to the output terminal of subtractor 32 and to the output terminal of memory 33 supplying a signal representative of the minimum admissible pressure in the left ventricle $P_{G\ mini}$.

Finally, the outputs of comparators 34,35 are connected respectively to the two inputs of a power amplifier 38 whose output controls the motor 20 of pump 19, whereas the two outputs of comparators 36,37 are connected respectively to the two inputs of a power amplifier 39 whose output controls the motor 22 of the pneumatic distributor 21.

Of course, a man skilled in the art may infer, from the diagram of the device 17 of FIG. 2, equivalent diagrams for the devices 17 of FIG. 4, 17'' of FIG. 4 and 14''' of FIG. 5.

As is evident and as it follows moreover already from what has gone before, the invention is in no wise limited to those of its modes of application and embodiments which have been more especially considered; it embraces, on the contrary, all variations thereof.

I claim:

1. A sequential pneumatic control device implantable in the human body and supplied with electrical energy, for use at least with a pneumatically operated cardiac prosthesis of the type formed by a biventricular monobloc assembly said control device comprising:

at least one housing forming an enclosure for a drive gas reserve, said housing comprised of an open rigid case having at least one opening therein and a wall, said wall being at least partially flexible and sealingly connected to said case such that said wall is subjected to flexing by the internal pressures of the human body and forms a flexible pocket, and such that the gas reserve is formed partly by said open rigid case and partly by said flexible pocket;

a motor mounted in said housing;

a pneumatic pump mounted in said housing and driven by said motor;

at least one main valve mounted in said housing for distributing the pressurized gas delivered by the pump to a device output port;

at least one electric motor mounted in said housing for actuating said valve;

a reference pressure detector;

a detector means for receiving a signal responsive to a cardiac condition; and control means mounted in said housing and having inputs connected to said reference pressure detector and said detector means and having outputs connected to the motors of the pneumatic pump and of the valve.

2. The device according to claim 1, characterized in that the control means (17, 17'', 17''') are electronic and in that said detector and detector means are adapted to deliver electric signals.

3. The device according to claim 2, characterized in that it comprises means for supporting the flexible part of the wall of the reserve comprising a semi-rigid dividing wall; and in that the electric circuits of said device are carried by said dividing wall, said dividing wall comprised of a printed circuit board.

4. The device according to claim 2, characterized in that it comprises means for supporting the flexible part of the wall of the reserve comprising a rigid dividing wall, and in that the electronic circuits of said device are carried by said dividing wall, said dividing wall comprised of a printed circuit board.

5. The device according to claim 3 and further comprising an auxiliary valve controlled by said control means, said auxiliary valve connected in parallel across said main valve and cyclically connected said pneumatic pump to said device output port such that a total cardiac prosthesis when connected to said output port is suppoed from the gas reserve.

6. A sequential pneumatic control device implantable in the human body and supplied with electrical energy, said device for use at least with a pneumatically operated cardiac prosthesis of the type formed by a biventricular monobloc assembly, said control device comprising a housing which forms an enclosure for a drive gas reserve, said housing comprised of:

an open rigid case having at least one opening therein;

a wall; and means for sealingly connecting said wall to said rigid case to form a flexible pocket in communication with said opening such that said wall is at least partially flexible but non-resilient so that when said device is implanted in the human body, said wall adds no additional forces to the internal pressures of the human body but rather said wall is flexed by the internal pressures of the human body, and so as to present a constant surface area thereto, wherein said gas reserve is formed partly by said open rigid case and partly by said flexible pocket.

7. The device according to claim 6, characterized in that it comprises support means (13) for maintaining the flexible part of the wall of the reserve extended when the amount of gas contained in the reserve is low.

8. The device as claimed in claim 6 wherein said wall is entirely flexible and non-resilient.

* * * * *